United States Patent [19]

Tenmyo

[11] Patent Number: 5,563,670
[45] Date of Patent: Oct. 8, 1996

[54] OPTICAL APPARATUS HAVING A FUNCTION TO ADJUST THE DIOPTER

[75] Inventor: Yoshiharu Tenmyo, Yokohama, Japan

[73] Assignee: Canon Kabushiki Kaisha, Tokyo, Japan

[21] Appl. No.: 357,647

[22] Filed: Dec. 16, 1994

[30] Foreign Application Priority Data

Dec. 24, 1993 [JP] Japan .................. 5-327547

[51] Int. Cl.⁶ .................. G03B 13/02; A61B 3/10
[52] U.S. Cl. .................. 396/373; 351/211
[58] Field of Search .............. 354/62, 219; 351/210–212

[56] References Cited

U.S. PATENT DOCUMENTS

| | | | |
|---|---|---|---|
| 4,181,408 | 1/1980 | Senders | 351/210 X |
| 4,300,818 | 11/1981 | Schachar | 351/210 X |
| 4,402,325 | 9/1983 | Sawa | 351/210 X |
| 4,431,278 | 2/1984 | Nohda | 351/211 |
| 4,619,505 | 10/1988 | Hache et al. | 351/211 |
| 4,828,381 | 5/1989 | Shindo | 351/211 |
| 4,889,422 | 12/1989 | Pavlidis | 351/210 |
| 5,071,245 | 12/1991 | Fukuma et al. | 351/211 |
| 5,182,443 | 1/1993 | Suda et al. | 354/219 X |
| 5,225,862 | 7/1993 | Nagano et al. | 354/62 |

FOREIGN PATENT DOCUMENTS

| | | |
|---|---|---|
| 0283749 | 9/1988 | European Pat. Off. . |
| 63-206731 | 8/1988 | Japan . |
| 1-241511 | 9/1989 | Japan . |
| 2-252432 | 10/1990 | Japan . |
| 4-31690 | 5/1992 | Japan . |

*Primary Examiner*—W. B. Perkey
*Attorney, Agent, or Firm*—Fitzpatrick, Cella, Harper & Scinto

[57] ABSTRACT

An optical apparatus having an improved function to adjust the diopter thereof. The optical apparatus includes an observation optical system and a control device for detecting information relating to an age of an eye and controlling the optical system based on the detection result.

12 Claims, 11 Drawing Sheets

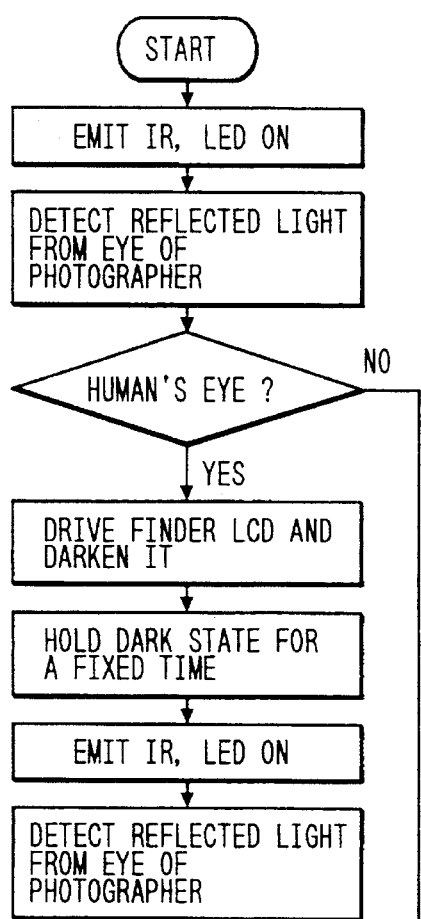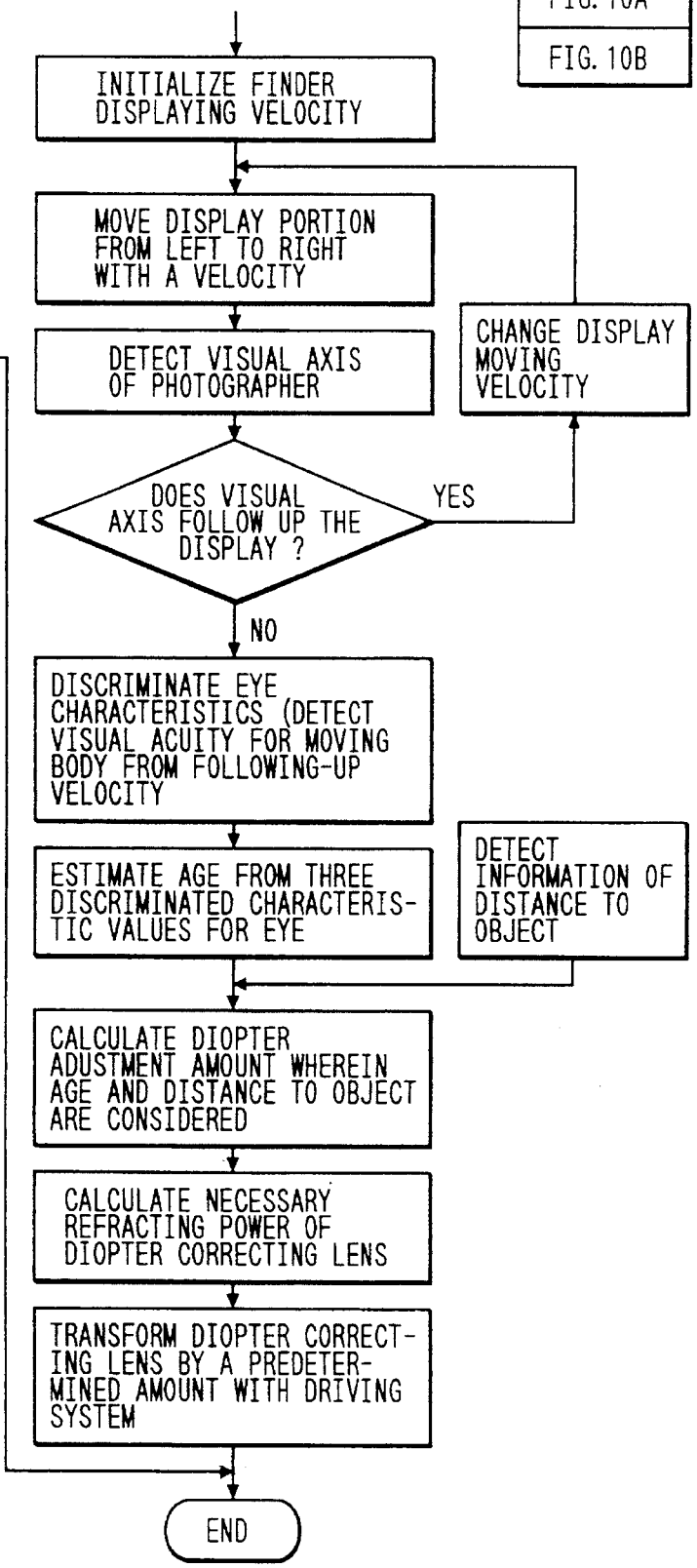
FIG. 10A
FIG. 10
| FIG. 10A |
| FIG. 10B |

OPTICAL APPARATUS HAVING A FUNCTION TO ADJUST THE DIOPTER

BACKGROUND OF THE INVENTION

1. Field of the Invention

The present invention relates to an optical apparatus, such as a camera having a function to adjust the diopter, which can correct the diopter, taking characteristics of photographer's eye into account.

2. Related Background Art

There is an apparatus which detects the refractivity of the eye of a photographer and automatically corrects the diopter of the apparatus, based on a value of the detection.

Such an apparatus, however, uses an eye refractometer provided as detecting means for detecting the amount of correction of the diopter, in a finder, which causes the following problems.

(1) The eye refractometer is very expensive because the refractometer requires a high-luminance LED, a special coating on its lens, and a high-precision photo sensor for detecting a position.

(2) Diopter adjustment with an eye refractometer consumes a lot of energy and has a long setting time. Since accurate diopter detection cannot be made unless the measurement by the eye refractometer is continued throughout the period of taking a picture, the emission time of the high-luminance LED becomes longer, which increases dissipation power. Also, because the position for correcting the diopter is determined while accommodation of the person and diopter adjustment by a mechanical drive are alternately repeated, some time is necessary for completely correcting the diopter and excessive energy is dissipated for driving the lens.

(3) When the eye refractometer is set inside a camera it is difficult to obtain high accuracy. Since the reflectivity at the retina is as low as 0.2% incident light from unnecessary portions (ghosts) becomes problematic for detection. However, different from eye refractometers for exclusive use as refractometers, the finder is set near an eyepiece portion, where incident light from the outside is inevitable (particularly, in the case of wearers of glasses, where the influence of external incident light is great because of the long distance between the eyepiece portion and the eye). It is thus difficult to perfectly remove ghosts. Also, because the external light is incident directly into the eye, the diameter of the pupil becomes narrower when the outside is bright, thereby making accurate measurement of eye refractivity difficult.

SUMMARY OF THE INVENTION

An object of the present invention is to provide an optical apparatus having an improved function to adjust the diopter thereof.

According to a first aspect, the present invention comprises an apparatus comprising an observation optical system and control means for detecting information relating to an age of the eye and controlling the optical system based on the detection.

According to a second aspect, the present invention comprises an apparatus comprising an observation optical system and control means for detecting whether the eye has presbyopia or not and controlling the optical system based on the detection.

According to a third aspect, the present invention relates to an apparatus comprising a finder and control means for detecting information relating to whether the age of an eye looking into the finder is high or low and controlling the optical system based on the detection, thereby adjusting the diopter thereof.

According to a fourth aspect, the present invention relates to an apparatus comprising a finder and control means for detecting whether an eye looking into the finder has presbyopia or not and controlling the optical system based on the detection, thereby adjusting the diopter thereof.

The control means noted above detects whether the age is high or low or whether the eye is presbyopia or not, based on at least one out of a diameter of the pupil, the change amount of the diameter of the pupil, the changing speed of the diameter of the pupil, the reflectivity of the pupil, the visual acuity for detecting a moving object, and the radius of curvature of the cornea of the eye.

DETAILED DESCRIPTION OF THE PREFERRED EMBODIMENTS

Figure 1:
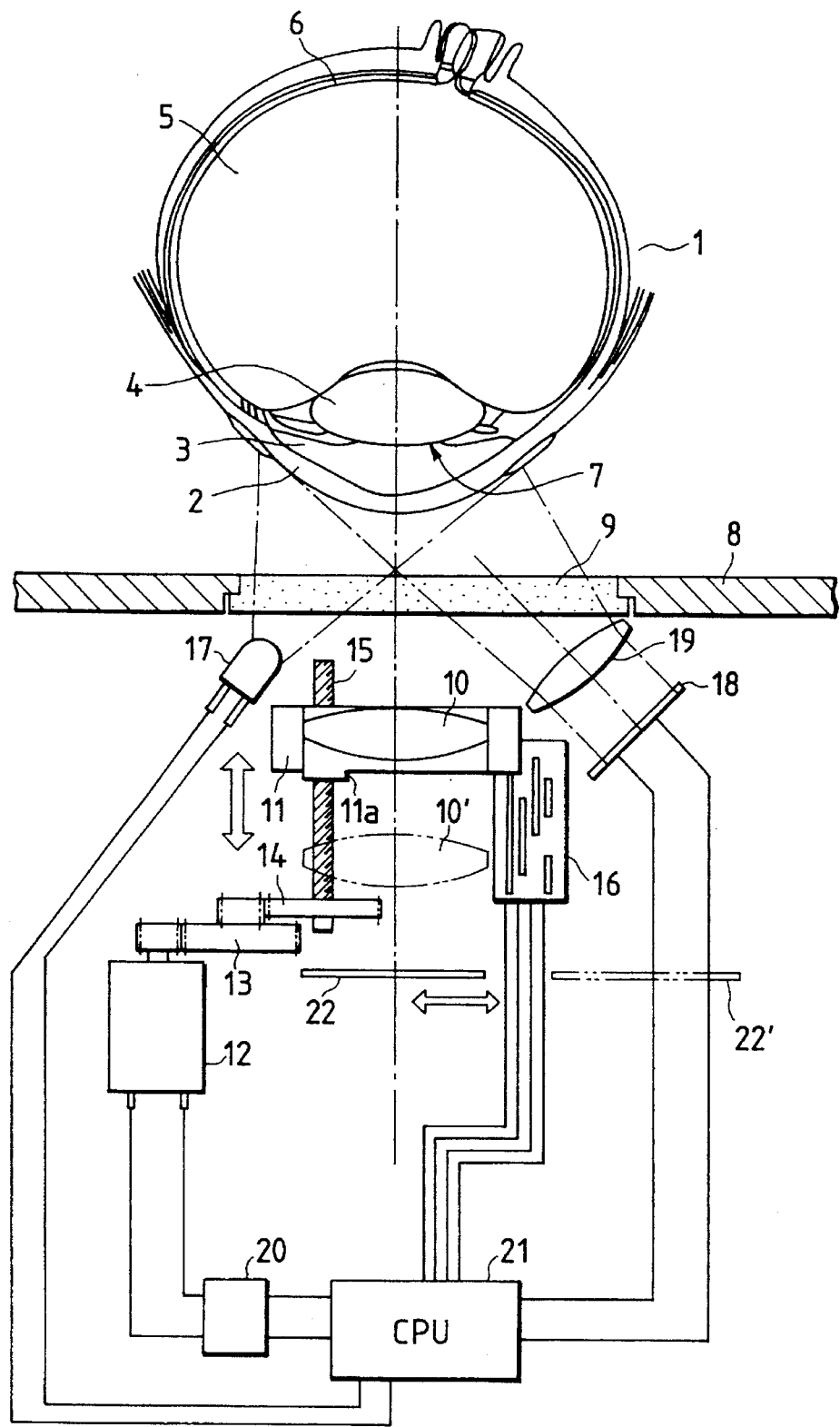
FIG. 1 is a drawing to show a state where a photographer is looking into a finder in a first embodiment of the present invention.

FIG. 1 shows the first embodiment of the present invention, wherein a photographer is looking into a finder of camera. Since the other parts of camera are well known, they are omitted and will not be discussed.

In FIG. 1, reference numeral 1 designates an eye of the photographer, and rays from the external field are incident on the cornea 2, made of a transparent body, and pass through transparent media of the anterior chamber liquid 3, the lens 4, and the vitreous body 5 to reach the retina 6.

Numeral 7 denotes the pupil, which is a hole surrounded by a portion of the pupil abundant in dye, called as the iris, and which corresponds to the aperture of camera. The pupil 7 is narrowed by the sphincter muscle of pupil and is expanded by the dilator muscle.

Further, numeral 8 denotes a cover of the camera body, 9 denotes an eyepiece window made of a transparent resin and set in a finder eyepiece portion, and 10 denotes a finder eyepiece lens. The eyepiece lens 10 is held by an eyepiece lens holding frame 11 and is controlled to move along the optical axis of finder optical system by a guide member provided in the camera body (not shown).

Numeral 12 is a motor for driving the eyepiece lens holding frame 11, the power of which is transmitted in such a manner that after a rotating speed of motor is reduced through a reduction gear 13, the power is transmitted to a final reduction gear 14. The reduction gear 14 has a helicoid portion 15 formed for moving the eyepiece lens holding frame 11 to a selected position, and the helicoid portion 15 is meshed with an engaging portion 11a provided in the eyepiece lens holding frame 11, whereby the eyepiece lens can be moved to the selected position. The motor 12 and reduction gears 13, 14 all are fixed to the camera body (not shown).

Numeral 16 is a position detecting board for detecting the position of the eyepiece lens 10, which is arranged to detect an absolute position of the eyepiece lens 10, using a position detection contact segment, not shown, fixed on the eyepiece lens holding frame 11.

Numeral 17 denotes an infrared LED for detecting characteristics of the photographer's eye, which is adjusted as to the optical axis center and a distribution of light so that the entire pupil is uniformly illuminated with light at a position where the photographer is observing an image in the field of finder. Although the example of the drawing shows only the LED, a condenser lens or a diffusion plate may be set in front of the LED as necessary.

Numeral 18 denotes a light-receiving element for receiving light resulting from reflection of the light from the infrared LED 17 on the photographer's eye, and 19 denotes a condenser lens for condensing the reflected light.

Numeral 20 is a motor driver for driving the motor, and 21 denotes a microcomputer for automatically controlling the diopter adjustment while detecting the characteristics of eye. Here, it is assumed that the infrared LED 17, the light-receiving element 18, and the condenser lens 19 are fixed to the camera body (not shown).

Numeral 22 is a light-shielding or light-reducing member arranged as capable of going into or out of the finder optical path, which is arranged as movable in the directions of the arrow as shown.

In the above structure, first, when well-known eye detecting means detects that the photographer holds the camera in position, the camera operates in a mode for detecting the characteristics of the photographer's eye. This eye characteristic detection mode is described below.

First, with the start of this mode, the light-shielding or light-reducing member 22 is inserted into the optical path of the finder optical system to temporarily keep the inside of the finder below a certain constant brightness. After a lapse of a time for which the diameter of the photographer's pupil can sufficiently expand, the infrared LED 17 is turned on to illuminate the photographer's pupil with uniform light. Reflected light from the pupil is collected by the condenser lens 19 set opposite to the LED 17 with respect to the finder optical axis, and is received by the light-receiving element 18 formed with a flat reception surface. The received light pattern at this time is such that a portion corresponding to the pupil has a little reflected light, because rays go into the eyeball, while a portion corresponding to the iris around the pupil has a lot of reflected light.

Detecting an area or a diameter of the portion with less reflected light, the diameter of the pupil can be detected in a state where the finder is dark (which is a state where the quantity of incident light into the pupil is small). Then the light-shielding or light-reducing plate 22 described above is withdrawn out of the optical path of the finder optical system. Namely, the light-shielding or light-reducing plate is moved to the position of 22' in FIG. 1. This movement of the light-shielding or light-reducing plate 22 changes the image in finder so as to allow a normal object to be observed. In this state, it is determined if the photometric value of the object is in a state of high luminance over a predetermined value. If the photometric value is not less than the predetermined value, nothing is done. If it is below the predetermined value, a separate light source not shown is turned on to make the photographer's eye receive light over the predetermined value. After a lapse of a time sufficient for the diameter of the pupil of the photographer's eye to change, the size of the pupil is again detected. In other words, the infrared LED 17 is turned on and reflected light thereof is detected by the light-receiving element 18. The two detections of the pupil diameter provide a change in the pupil diameter due to a change in luminance of the external field. Next, the above serial detection results of the pupil diameter are input into CPU 21, which determines the characteristics of the photographer's eye, particularly the photographer's age. For example, if the pupil diameter $\phi$ herein is 2.0 under brightness below the predetermined luminance value and also 2.0 under brightness over the predetermined luminance value, which should be normally changed, it can be determined that the photographer's eye shows no change of the pupil diameter for the change of brightness, that is, that the photographer's eye suffers from presbyopia. After the age is estimated from the characteristics of the photographer's eye as described, the diopter correction is next carried out according to the characteristics of the eye.

Figure 8:
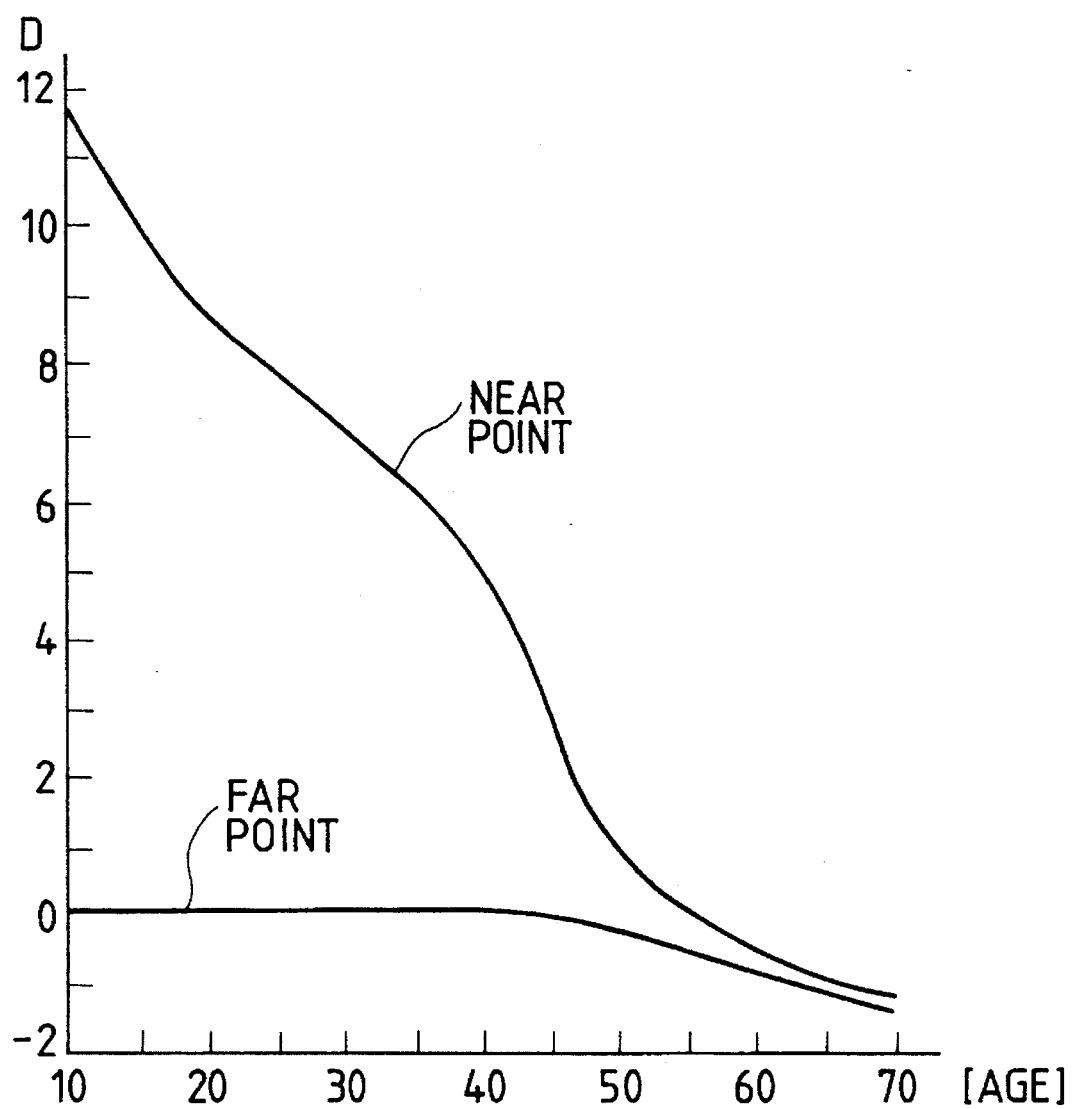
FIG. 8 is a drawing to show a change in the accommodation range of eye depending upon age.

For example, supposing, as described above, that the photographer's eye is determined as suffering from presbyopia. The diopter first needs to be corrected, because the eye having presbyopia is likely to have hyperopia, as shown in FIG. 8. The diopter normally used in the finder of the camera, etc., is often set at −1 diopter (D), taking into account the instrumental myopia, which is a phenomenon that the eye becomes myopic only while it looks into the eyepiece lens of optical instrument. The example of FIG. 1 shows the position of the eyepiece lens in this state at reference numeral 10'.

In contrast, if the photographer's eye has presbyopia as in the present embodiment, it is likely to have hyperopia. Then, the eyepiece lens needs to be moved toward the photographer's eye up to a position 10 shown by the solid line in FIG. 1, or the diopter needs to be corrected to the plus side. Although it depends upon individual differences between photographers, an amount of the correction should be an adjustment amount of about +0.5 to +1.0 diopter, as seen from FIG. 8.

Figure 9A:
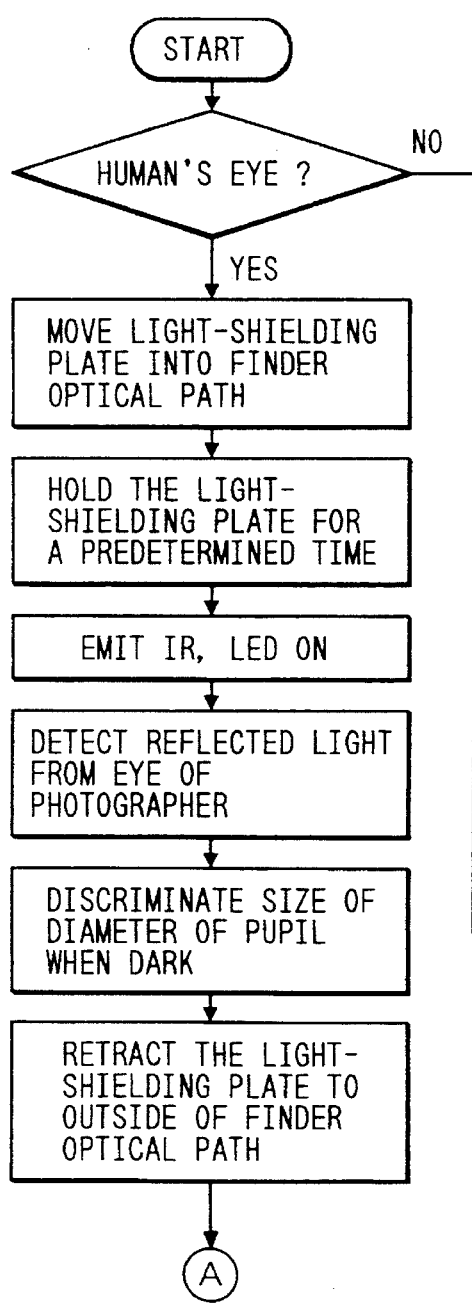
FIG. 9 is comprised of FIGS. 9A and 9B showing flowcharts of the first embodiment of the present invention.
Figure 9:
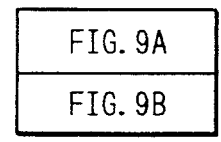
Figure 9B:
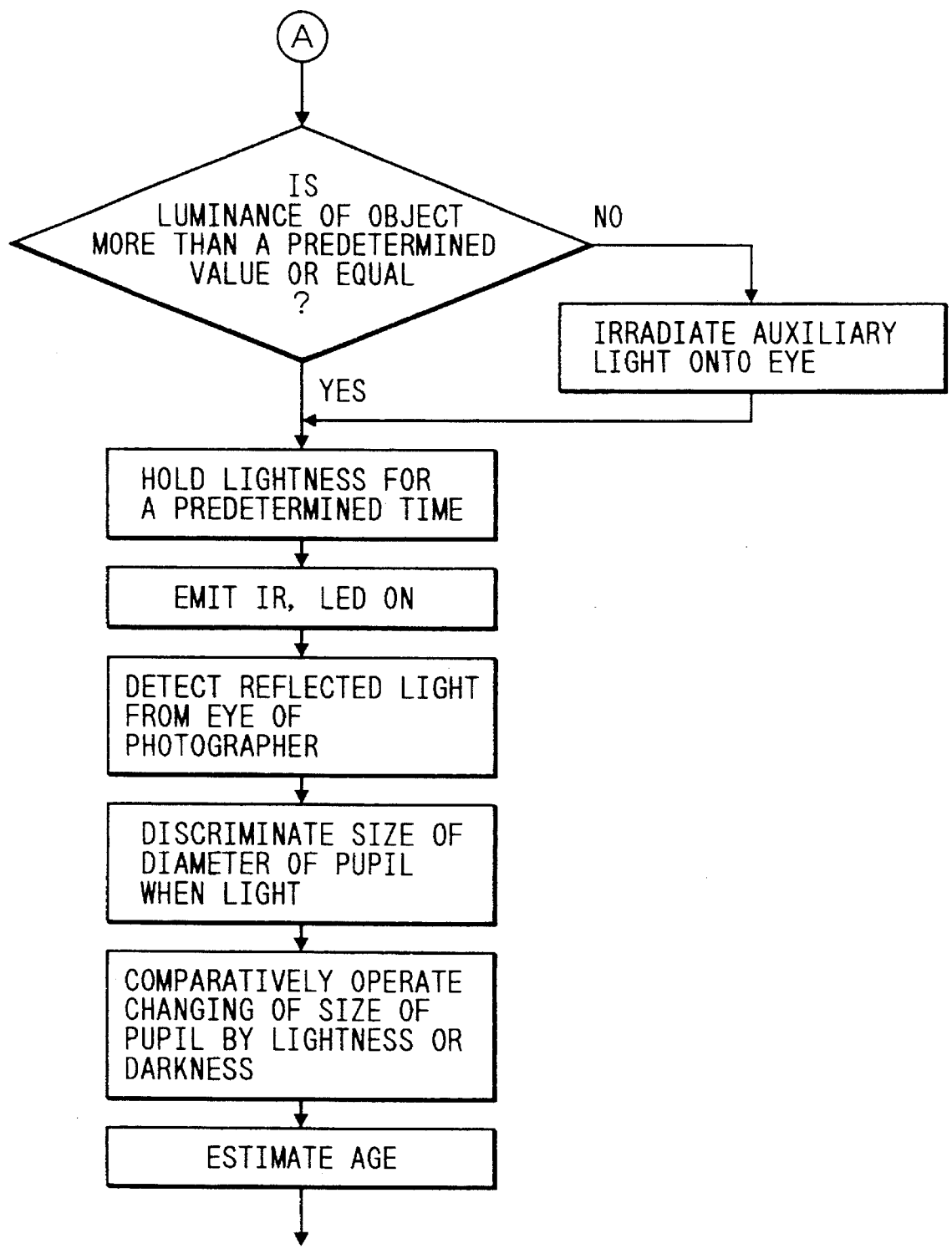

In FIG. 1, after the correction amount is calculated in CPU 21, the power is supplied through the motor driver 20 to the motor 12, and an output of the motor is transmitted through the reduction gear train 13 to drive the gear 14, whereby the helicoid portion 15 formed on the gear 14 moves the eyepiece lens holding frame 11 along the optical axis of the finder. An amount of the movement is detected by the position detection contact segment (not shown) and the position detection board 16, and then the power supply to the motor 12 is interrupted to stop the motor after completion of the necessary adjustment of the diopter. The above serial operations can automatically correct the diopter in accordance with the photographer's age. FIGS. 9A and 9B show a flowchart of the serial operations.

The present embodiment is so arranged that the age, particularly whether the patient has presbyopia or not, is determined based on the change in the pupil diameter due to the change of brightness, but characteristics changing with age of the eye may include some other types of factors as well as the change in the pupil diameter, and, therefore, accurate and fine estimation of age can be possible by detecting some of such factors. Below described are the phenomenon of presbyopia and the change in characteristics of the eye depending upon age, whereby the validity of the method for detecting the characteristics of the eye is described, which is the feature of the present invention.

The presbyopia is caused by the phenomenon of a diminishing of the visual functions, especially by a drop in the accommodation function to form images of objects at different distances on the retina. Thus, a means for correcting the presbyopia has been developed which uses eyeglasses to correct the refracting power of the eyeball optical system for forming an image of an object at infinity on the retina, into a normal state. However, because it is not a means for compensating for the original drop in the accommodation function, the near distance range goes out of the accommodation range with the eyeglasses on. Therefore, a person with presbyopia was previously required to take off the eyeglasses or to wear another eyeglasses in order to look at an object at a near distance.

FIG. 8 shows a quantitative change of the accommodation power of the eye depending upon age. In FIG. 8, the axis of the ordinate represents the accommodation power of eye in diopters (D). This unit is defined as a reciprocal of a distance from the object point focused on the retina to the object principal point of the eyeball, expressed in meters. The axis of the abscissa represents the age. In the drawing, "far point" indicates a distance where the in-focus state is naturally achieved without accommodation, and "near point" represents a distance where the eye is in focus on the closest point with the accommodation of eye. Here, the range between the far point and the near point is called the area of accommodation or the amplitude of accommodation. Also, the degree of accommodation of each person from the far point to the near point is called the accommodation power of that person. It is seen that the accommodation power decreases with age mainly because of hardening of the lens and that the distance of the near point becomes longer than the distance of the so-called photopic vision (25 to 30 cm).

Accordingly, for a person suffering presbyopia to take pictures without eyeglasses, at least the following two corrections are necessary.

(1) If a diopter change is caused at least over the accommodation power (amplitude) of the person with presbyopia, a short amount is automatically compensated for by the focus means of the finder.

(2) The hyperopia tendency specific to the presbyopia is corrected when the person is determined to have presbyopia.

Here, (1) would be a specific problem especially for cameras provided with an external finder and being capable of high-magnification zooming. Thus, it is necessary to detect a diopter change caused by a temperature change or a change in the distance to the object and to perform fine diopter correction when the detection value exceeds a predetermined value. Also, (2) is nothing but the first embodiment of the present invention.

Next described is an age change of the characteristics of eye. The following factors are considered as the characteristics of eye, particularly the characteristics gradually changing with age (and also being easy to detect).

(1) Distance (anterior chamber) between the cornea 2 and the lens 4; which is longest at about twenty years of age and is shorter for babies and the aged. The distance changes in the range approximately of 4.2 mm to 2.4 mm.

(2) Pupil diameter; which is, in a normal state, 2 mm in diameter for neonates and the aged, and 4 to 6 mm in diameter for adults and which changes depending upon brightness. Also, the pupil diameter changes depending not only on the light quantity but also on one's emotion or the stimulus one recieves via sympathetic nerve.

(3) The cornea tends to be flattened with age.

(4) Change in shape of lens 4; the curvature of the front surface of the lens increases, because deformation by the muscular system cannot be effectively carried out with age. (However, the change in shape upon focusing becomes smaller.)

(5) Insoluble protein forming the lens increases with age, (which decreases the refractive index of the entire lens) which increases light diffusion at interfaces in the multi-layer structure, thus lowering the sharpness of the image formed thereby.

(6) A change of visual acuity for a moving object with age; which is a phenomenon that the eyes naturally move unconsciously, when one is watching an external view through a window of a moving vehicle. This is called optokinetic nystagmus. The change of visual acuity for viewing a moving object changes with age. The visual acuity for viewing a moving object is lowered with age.

(7) As age increases, the gel vitreous body starts becoming liquefied, which weakens the function of holding the spatial arrangement of the eyeball optical system. This is also related to (1) and (3).

As described above, the characteristics of the eye gradually change with age. This tendency is nearly consistent except for more or less individual differences. It is thus possible to accurately estimate the age by detecting some of the listed characteristics to quantitatively measure change amounts thereof.

For example, as for the detection of the pupil diameter shown in the first embodiment, the changing speed of the pupil diameter may be detected as well as the simple change amount of the pupil diameter due to brightness, whereby a change of reflex speed with age or a degree of asthenopia can be detected so as to enhance accuracy. Conversely, in order to make the detection mechanism simpler, the age may be estimated by detecting the size of the pupil diameter only under brightness below a certain predetermined value.

Although the above embodiment is so arranged that the light projecting and receiving systems for detecting the characteristics of eye are set near the finder optical system (left and right), the light projection and receiving systems do not always have to be limited to this arrangement. For example, it is also possible that part of the finder optical system is optically split and the light receiving system or the light projection and receiving systems are set therein. This can reduce errors of the detection system even in a state where the photographer's eye is away from the finder, thus realizing a more effective detection system.

Figure 2:
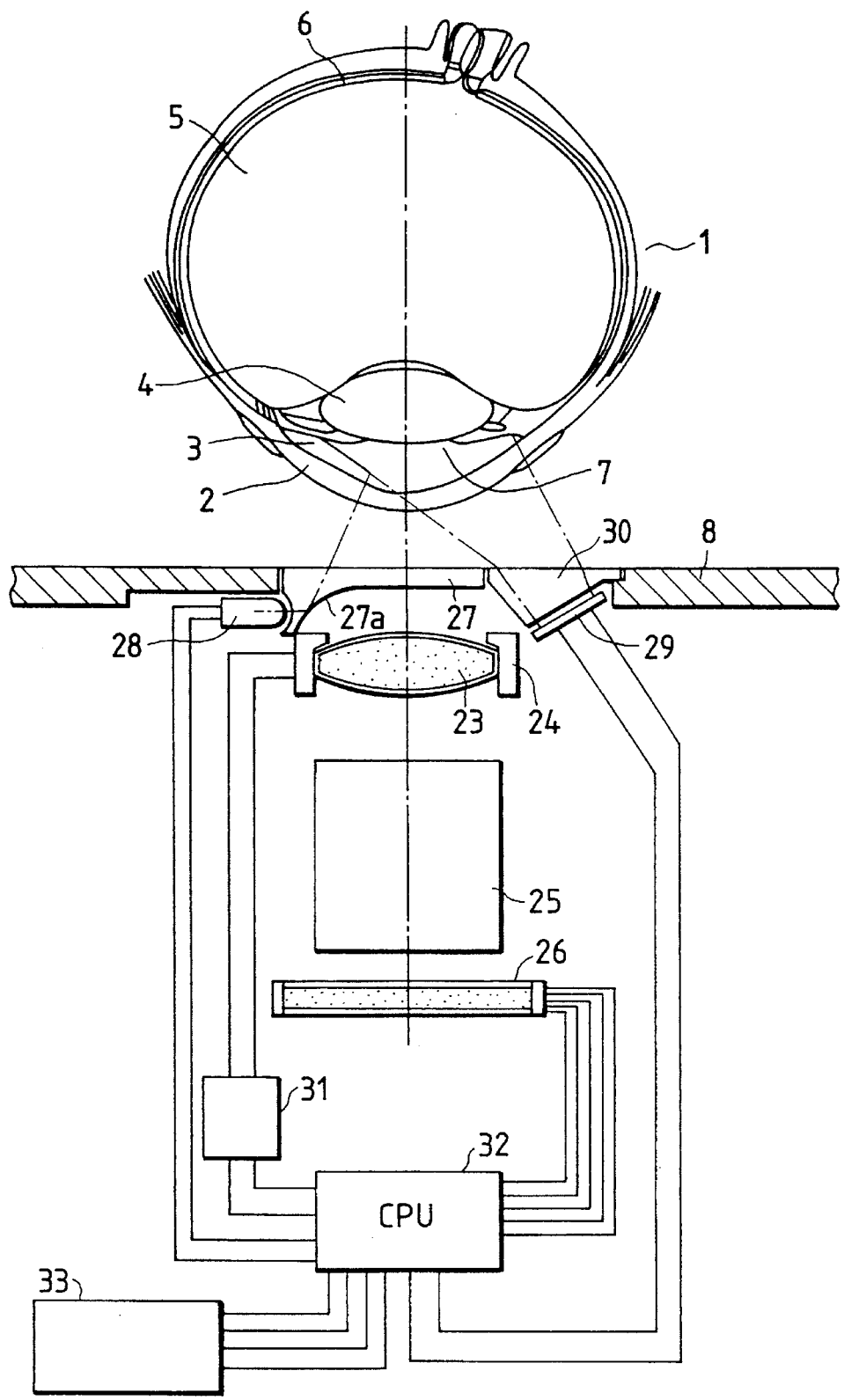
FIG. 2 is a drawing to show a state where a photographer is looking into a finder in a second embodiment of the present invention.

FIG. 2 shows the second embodiment of the present invention, wherein the photographer is looking into the finder of camera. The same portions as those in FIG. 1 are denoted by the same reference numerals. A feature of the present embodiment is that there is no moving part for adjusting the diopter of the finder. Another feature is that the finder system is an external finder system of a real image type provided independently of the photo-taking system. The second embodiment will be described with reference to the drawings.

Reference numeral 23 designates an eyepiece lens constructed of a focal length variable lens. Namely, the eyepiece lens 23 is constructed in such a manner that the inside thereof is charged with a high-index liquid and that the shape of the lens, particularly the shape of curved surfaces, can be deformed with a pressure from the outside so as to change the focal length of the lens. Numeral 24 denotes an eyepiece lens holding frame which holds the eyepiece lens 23 and which can change the shape of the eyepiece lens by pressing at least a part of the periphery of the eyepiece lens 23. Numeral 25 is a Porro prism for inverting an image in a finder, and 26 denotes a transmission-type liquid crystal device located at a focal point (an object image) of a finder objective lens and nearly at a position of the focal point of eyepiece lens 23, which can display various indications for the camera, such as an AF indication, a parallax correction indication, etc., and which can display a pattern for detecting the characteristics of photographer's eye and can adjust the brightness thereof.

Numeral 27 is an eyepiece window made of a transparent resin for protecting the eyepiece lens 23, provided in the finder eyepiece portion, and 27a denotes a prism portion formed in a part of the eyepiece window. Numeral 28 is an infrared light emitting diode, and 29 denotes a light-receiving element for detecting reflected light from the eye. Numeral 30 denotes a prism for detecting the reflected light from the photographer's eye, disposed in front of the light-receiving element 29. The prism 30 is separate from the eyepiece window 27 and is subject to a treatment of black painting or the like in order to prevent the light from the infrared light emitting diode from being incident directly thereinto.

Numeral 31 is a drive unit for pressing the eyepiece lens holding frame 24 in the radial direction of lens, and 32 denotes a microcomputer for controlling the optical systems for detecting the characteristics of photographer's eye and for automatically correcting the diopter. Further, numeral 33 is an element for giving the finder a diopter change, for example a detecting device for detecting the distance to an object etc.

Next described is the operation of the second embodiment as so arranged.

When the photographer looks into the finder of camera, the infrared LED 28 first emits a light beam and the light-receiving element 29 detects reflected light thereof. When recognition of a pattern of the reflected light assures the device that there is a human eye present, the camera goes into the mode for detecting the characteristics of photographer's eye. This eye characteristic detection mode is next described.

Figure 3A:
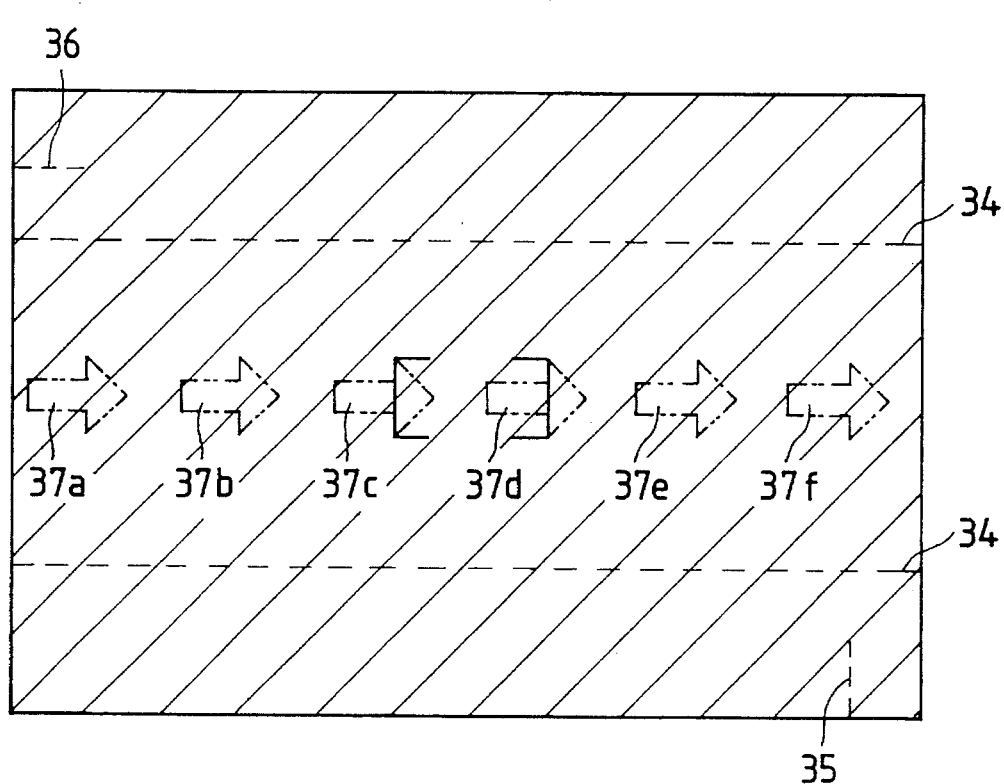
FIGS. 3A and 3B are drawings to show indications in the finder of the second embodiment of the present invention.

When this mode starts, the liquid crystal device 26 set at the focus position of the finder optical system is first activated to keep for a certain constant time a state in which the brightness in the finder is not more than a predetermined value but is sufficient to fully open the pupil of a young person. FIG. 3A shows a state of display in the finder at this moment, wherein indications on the finder are in an off state and therefore the entire field looks dark. Describing the indications in the finder as shown, 34 represents a display portion for a panorama, 35 and 36 display portions for parallax correction, and 37a to 37f display portions for detecting the visual acuity for moving object, of eye.

Figure 4A:
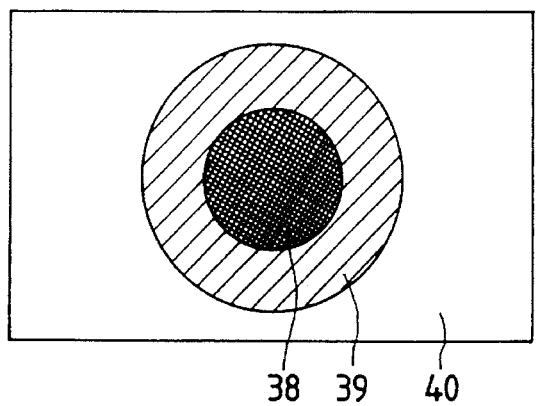
FIGS. 4A, 4B, 4C, and 4D are explanatory drawings to illustrate detection results of characteristics of eye on a photo sensor in the second embodiment of the present invention.
Figure 4B:
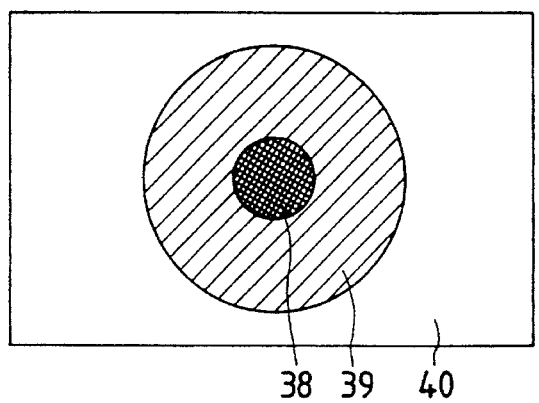
Figure 4C:
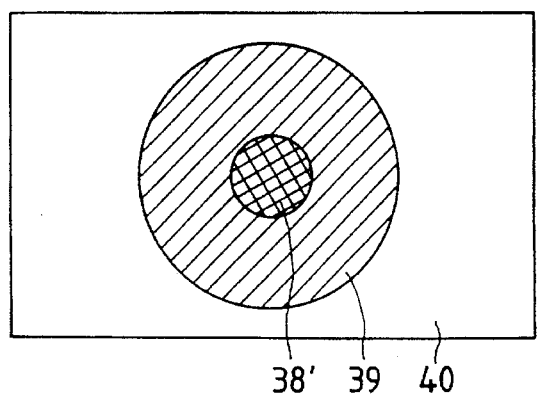

FIGS. 4A and 4C briefly show for explanation of detection results of the characteristics of eye on the light-receiving element 29 in this state. FIG. 4A shows a state of the pupil when a young person is looking into the finder kept at a brightness below the predetermined value, while FIG. 4C shows a pupil state for a person having presbyopia under the same conditions.

In the drawings, numeral 38 designates a portion where the amount of reflected light is small at the center of the eyeball, which corresponds to the pupil portion, and 39 denotes a portion corresponding to the iris portion where an amount of reflected light is almost as small. (These two portions constitute the black eye.) On the other hand, numeral 40 represents a portion where an amount of reflected light is largest, which corresponds to a portion of the white eye outside the black eye. In the drawings, the density of meshes is different between the portions 38, 38' corresponding to the pupil, which indicates that there is a difference in the quantity of reflected light per unit area between the portions corresponding to the pupil. The amount of reflected light is small with young people as shown in FIG. 4A, while an amount of reflected light per unit area is rather large with people having presbyopia as shown in FIG. 4C.

Figure 4D:
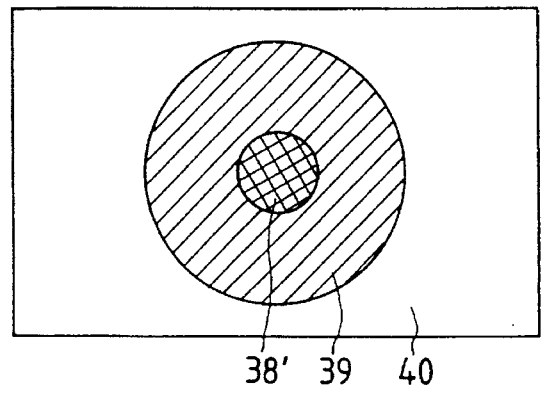

Next, the brightness in the finder is changed to above the predetermined value. Namely, the transmission-type liquid crystal device 26 is turned to a transmissive state. In this case, if the luminance of the object is too low to obtain sufficient brightness on the finder, an illumination apparatus not shown is activated to illuminate the transmission-type liquid crystal device 26 set at the focus position of finder, whereby the liquid crystal device can be kept at a brightness above the predetermined value before completion of detection of the eye characteristics. FIGS. 4B and 4D show the detection results of eye characteristics on the light-receiving element 29 in this state. FIG. 4B shows a state for young people, while FIG. 4D a state for people having presbyopia.

Next described are changes of characteristics of the photographer's eye, changing depending upon the adjustment of brightness in the finder as described. First described are the cases of young people as shown in FIGS. 4A and 4B. In FIG. 4A, showing the detection result in the dark state, the diameter of the pupil is sufficiently large ($\phi$: about 6). Further, the portion corresponding to the pupil is dark, which indicates that there is little light diffusion in the lens. On the other hand, in FIG. 4B showing the detection result in the bright state, the diameter of the pupil becomes smaller ($\phi$: about 2). As with FIG. 4A, the portion corresponding to the pupil is dark.

Next described are the cases for people having presbyopia as shown in FIGS. 4C and 4D. In FIG. 4C showing the detection result in the dark state, the diameter of the pupil is small ($\phi$: about 2) but the portion corresponding to the pupil is somewhat brighter than that in the case of young people, which means that a certain amount of light diffusion occurs in the lens. On the other hand, in FIG. 4D showing the detection result in the bright state, nothing is changed from the dark state. Thus, the diameter of the pupil is still small ($\phi 2$) and a certain amount of light diffusion still occurs in the portion corresponding to the pupil.

As described above, the characteristics of the eye change with age and therefore the age can be estimated to some extent from a change of pupil diameter or a state of diffusion of the lens depending upon brightness, or further from the speed at which the pupil responds to a change of brightness, etc.

Figure 3B:
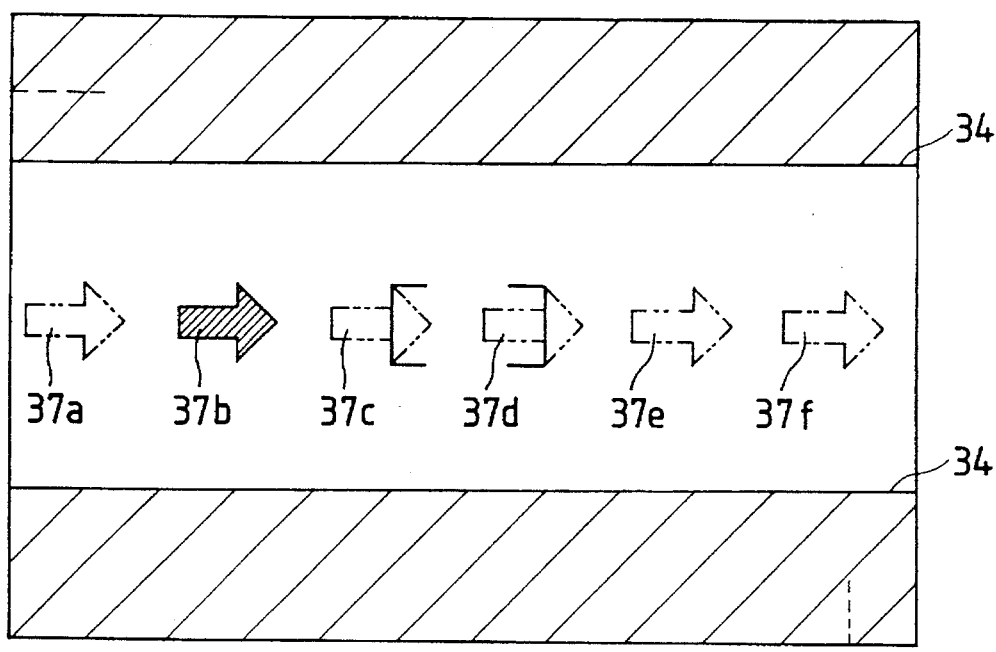

Next described with FIG. 3B and FIG. 5 is a method for measuring the visual acuity, for viewing a moving object, of a photographer.

Figure 5A:
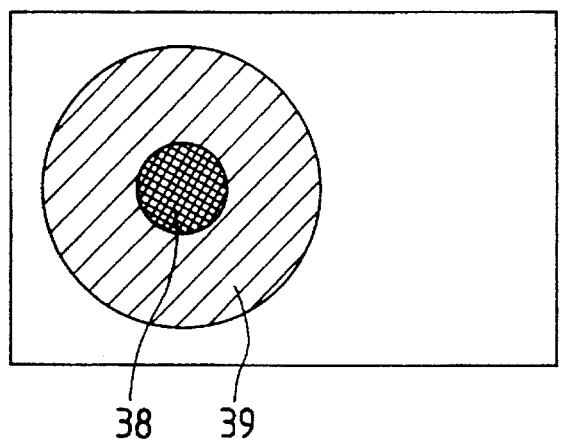
FIGS. 5A, 5B, and 5C are explanatory drawings to illustrate detection results of the motion of the eye in the second embodiment of the present invention.
Figure 5B:
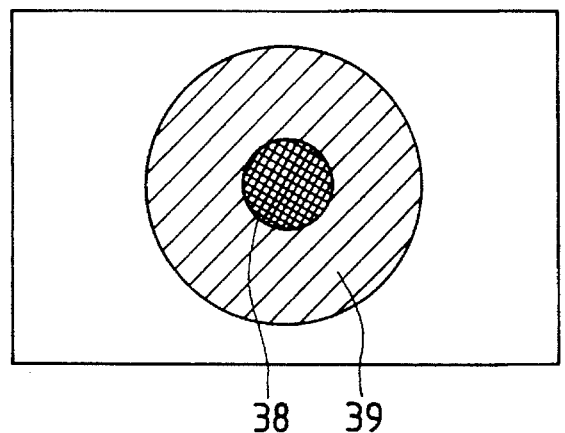
Figure 5C:
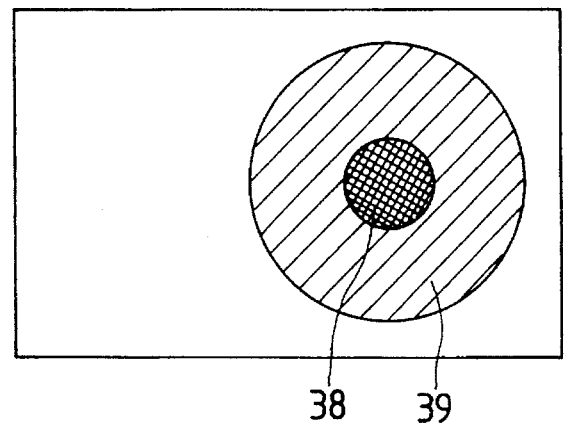

FIG. 3B shows a finder image upon detecting the visual acuity for viewing a moving object. In FIG. 3B, the field frame is set in a panorama state in order to reduce the influence of objects in the external field. Namely, portions above and below the panorama display portion 34, of the finder image are made dark by driving the transmission-type liquid crystal device 26 to control the transmittance thereof. This makes it easier to keep the visual axis of a photographer fixed in the central display portion. The display portions 37a to 37f of arrows provided at six locations in the central portion of screen are successively activated in this state. Namely, the left end indication 37a is first displayed, and then next indication 37b is displayed at the same time as the indication 37a is turned off. In this manner, indications are shifted one by one from the left indication to the right indication. Reaching the right end indication 37f, the display returns to the indication 37a. This operation is repeated at a constant display speed. FIG. 3B shows a displayed state of the second indication 37b. As the arrow indications are shifted one by one, the photographer observes them as if an arrow moves from left to right. The moving speed of the arrows can be changed. The purpose of this display is to determine if the visual axis of the eye can follow at the moving speed, that is, to detect the visual acuity for viewing moving object by adaptation to the speed. FIGS. 5A to 5C show states of detecting a motion (visual axis) of photographer's eye at this time. As in FIGS. 4A–4C, each drawing shows a state in which reflected light by eye, of the light reflected from infrared LED 28, is detected through an imaging lens (not shown) and the light-receiving element 29.

Corresponding to the movement of arrow indications as shown in FIG. 3B, the visual axis also moves successively from the left position shown in FIG. 5A, to the center shown in FIG. 5B, and then to the right position shown in FIG. 5C. In this case, depending upon age or fatigue of the eye, there would occur a state that, failing to follow up to the moving speed of arrows, the visual axis cannot catch up with the movement of the arrows (a state where the visual axis is fixed or a state where the eye is closed). Therefore, the age can be estimated by determining whether the visual axis is catching up with the moving speed of arrows, thereby detecting the visual acuity for viewing a moving object, of photographer.

After the characteristics of the photographer's eye are detected and the age is estimated by the above method, the diopter is corrected depending upon the age. Namely, in FIG. 2, an optimum diopter is calculated in CPU 32, taking into account a change in the amount of the diopter depending upon age, based on FIG. 8, and an output from the diopter change detecting apparatus 33 of the finder optical system. Based on the calculation value, the eyepiece lens holding frame 24 is pressed in the radial direction of the lens through the drive unit 31, whereby the eyepiece lens 23 is deformed into a shape to attain a desired refracting power, thus correcting the optimum diopter.

Figure 10B:
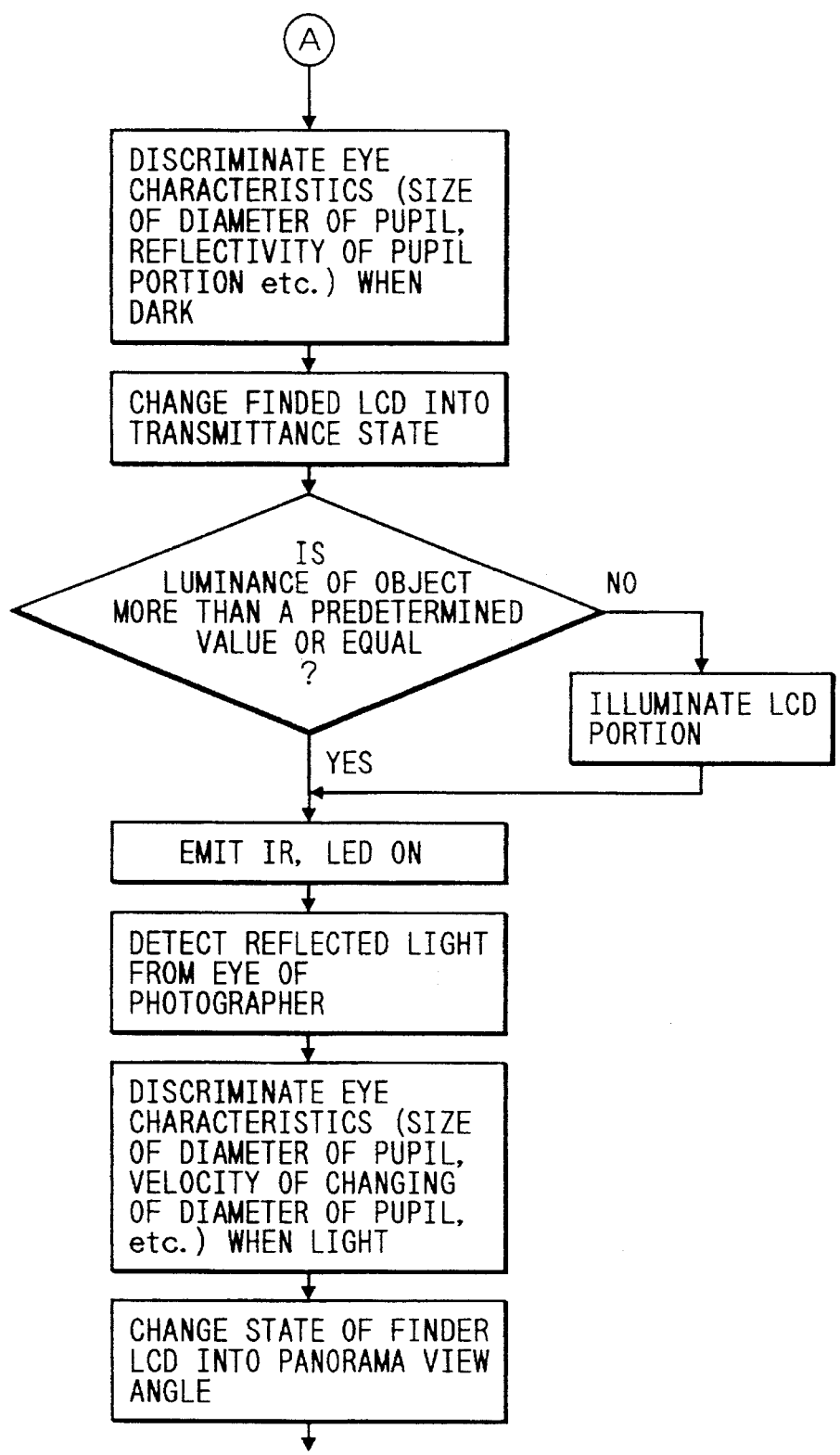
FIG. 10 is comprised of FIGS. 10A and 10B showing flowcharts of the second embodiment of the present invention.

The optimum diopter correction optimum for a photographer can be made by the above serial operations of the detection of the characteristics of eye to the lens deformation. FIGS. 10A and 10B show a flowchart of the serial operations. The eye detection method in the second embodiment included methods for detecting the change of the pupil diameter depending upon the brightness of photographer's eye, the change speed of the pupil diameter, the reflectivity in the pupil portion, the visual acuity for viewing moving object, etc., but it is by no means limited to the above methods. The detection method may be a combination of some methods among the above methods or a combination with another method. For example, the another method may be a measurement of the radius of curvature of the cornea etc. Also, the present embodiment was so arranged that the change of refracting power of the eyepiece lens for adjustment of, diopter was carried out by the change of the lens shape, but it is not always limited to this method. For example, the diopter change can be made without a moving part, using a lens utilizing a liquid crystal which changes the refractive index depending upon an applied voltage, which also improves space efficiency.

The arrow indications in the finder for checking the visual acuity for viewing a moving object in the above embodiment may be replaced by indications of an arbitrary shape without a need to be limited to the arrow indications. For example, movement of stripe patterns etc. may be employed. Also, as for the direction of movement, the movement does not have to be limited to the movement from left to right. Further, the display method is not limited to the liquid crystal, but it may employ such an arrangement that LEDs set near the finder image are selectively activated to emit respective light beams.

Another different feature of the present embodiment is that the light projection and receiving systems of the eye are arranged to have a plurality of functions. Namely, by the light emission of the infrared LED 28 and the light-receiving element 29 receiving the light, the following functions can be simultaneously detected.

(1) Eye detection: shape recognition of whether one located behind the camera eyepiece portion is a photographer's eye.

(2) Visual axis detection: used as detecting means in the cases where the visual axis is used as input means for setting of the focus point, setting of the shooting mode, etc.

(3) Eye characteristic detection for diopter correction: detection as described above in the embodiments, for example the diameter of the pupil, etc.

Further, the present embodiment employs the transmission type liquid crystal as the display means of finder information, and therefore, an important feature of the present embodiment is that this liquid crystal display is utilized to simultaneously perform the control of brightness in the finder for the detection of the eye characteristics and the pattern movement for detection of visual acuity for viewing a moving object.

Figure 6:
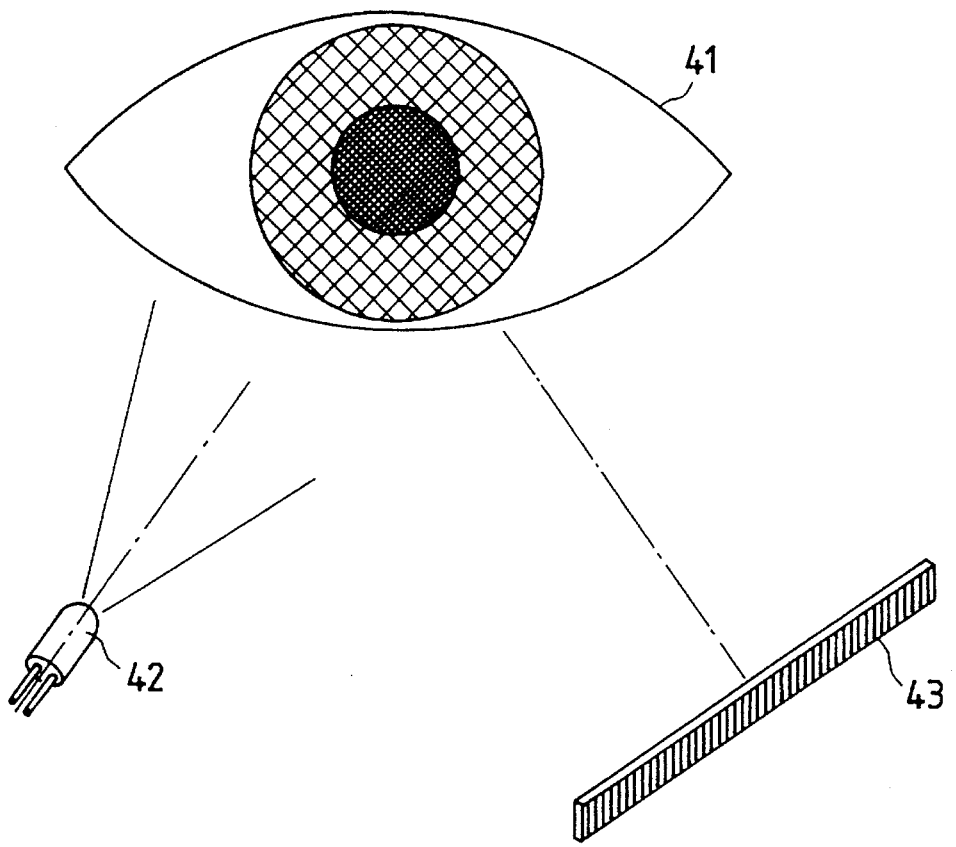
FIG. 6 is a drawing to show a detecting state of an eye in a third embodiment of the present invention.
Figure 7:
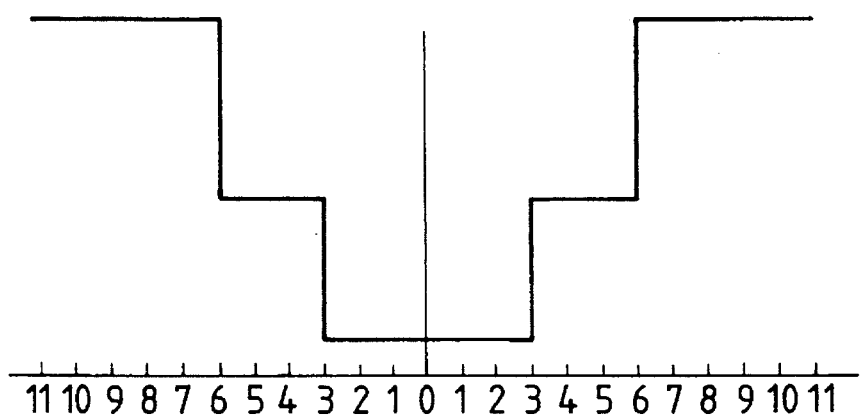
FIG. 7 is a drawing to show detection results of eye in the third embodiment of the present invention.

FIG. 6 and FIG. 7 show the third embodiment of the present invention.

The first and second embodiments show the methods for detecting the characteristics of the eye including the step of detecting the characteristics in a relatively wide region by the light-receiving element and a step of recognizing the pupil diameter from the detection value, which was accurate in detection but complicated in arithmetic processing up to the detection. The present embodiment shows a method for simply detecting the characteristics of the eye.

In FIG. 6, numeral 41 designates a photographer's eye, 42 denotes an infrared LED, and 43 denotes a line sensor.

Generally, cameras using an external finder are often miniaturization-oriented compact cameras and the shape of finder is made smaller. Because of this, an amount of, deviation of the eye (pupil diameter) to look over the entire region without an eclipse at the corner thereof is small when the photographer looks into the finder. Also, an amount in back and forth directions along the optical axis, i.e., the eye point is also short, so that the freedom to position the eye relative to the finder optical system is extremely limited. Therefore, the position of the photographer's eye relative to the finder eyepiece lens can be defined almost uniquely. Thus, the present embodiment is so arranged that the position of photographer's eye is preliminarily assumed and the age is estimated from the reflection characteristics of eye in the horizontal cross section through the optical axis center.

As shown in FIG. 6, the infrared LED 39 and the line sensor 40 are set relative to the assumed position of the photographer's eye on the horizontal cross section through the optical axis. Then, keeping the brightness in the finder below the predetermined value, the diameter of the pupil is enlarged. FIG. 7 shows an example of detection values thus obtained.

FIG. 7 is a drawing wherein the optical axis center of photographer's eye is set as 0, the axis of the abscissa represents the distance from the optical axis center, and the axis the ordinate represents a value of the reflected light quantity at each position. In the example as shown, the pupil diameter φ is 6 and the quantity of reflected light at that time can be simultaneously detected. The results show that the photographer is a young person. If the diameter of the pupil is small and the reflectivity of the portion corresponding to the pupil diameter is high, it can be determined that the photographer has presbyopia as in the first and second embodiments.

The diopter adjusting method after the age detection is the same as in the previous embodiments, and thus an explanation thereof is omitted. Since the present embodiment utilizes the line sensor as a light-receiving sensor, it has advantages of low production cost and easiness of arithmetic processing after detection.

As described above, the embodiments of the present invention are so arranged that the characteristics of photographer's eye are detected, the age is estimated from the detection results, and the diopter is automatically corrected to an optimum value according to the age, whereby the diopter can be automatically corrected even for people having presbyopia who are incapable of adjusting it and, even for young people, loads on eye can be reduced because no need for excessive adjustment. Also, because the method for detecting the eye characteristics does not utilize reflection on the retina as used in the eye refractometers, but detects reflection from an element closer to the outside of the eye, the method has advantages that the detection of eye characteristics is easy and that the apparatus can be constructed at a low cost. Also, it is easy to make the detection mechanism smaller or multi-functional.

What is claimed is:

1. An optical apparatus comprising:
    an observation optical system to be used by an observer; and
    control means for estimating the age of the observer and adjusting said observing optical system according to the estimated age.

2. The apparatus according to claim 1, wherein said control means changes a position along an optical axis, of an objective lens in said observation optical system to adjust the diopter thereof.

3. The apparatus according to claim 1, wherein said control means changes a focal length of an objective lens in said observation optical system to adjust the diopter thereof.

4. The apparatus according to claim 1, wherein said control means detects whether the age of the observer is high or low, based on at least one of the diameter of the pupil, the change amount of the pupil diameter, the change speed of the pupil diameter, the reflectivity of the pupil, the visual acuity for viewing a moving object, and the radius of curvature of the cornea, of the eye of the observer.

5. An optical apparatus comprising:
    an observation optical system to be used by an observer; and
    control means for discriminating whether the observer is old or not and adjusting the observing optical system according to the discriminated result.

6. The apparatus according to claim 5, wherein said control means changes a position along an optical axis, of an objective lens in said observation optical system to adjust the diopter thereof.

7. The apparatus according to claim 5, wherein said control means changes the focal length of an objective lens in said observation optical system to adjust the diopter thereof.

8. The apparatus according to claim 5, wherein said control means detects whether the eye of the observer has presbyopia or not, based on at least one of the diameter of the pupil, the change amount of the pupil diameter, the change speed of the pupil diameter, the reflectivity of the pupil, the visual acuity for viewing a moving object, and the radius of curvature of the cornea, of the eye of the observer.

9. An optical apparatus comprising:
    a viewfinder; and
    control means for estimating the age of an observer using the apparatus and adjusting the diopter of said viewfinder according to the estimated age.

10. The apparatus according to claim 9, wherein said control means detects whether the age of the observer is high or low, based on at least one of the diameter of the pupil, the change amount of the pupil diameter, the change speed of the pupil diameter, the reflectivity of the pupil, the visual acuity for viewing the moving object, and the radius of curvature of the cornea, of the eye of the observer.

11. An optical apparatus comprising:
    a viewfinder; and
    control means for discriminating whether an observer using said apparatus is old or not and adjusting the diopter of said viewfinder according to the discriminated result.

12. The apparatus according to claim 11, wherein said control means detects whether the eye of the observer has presbyopia or not, based on at least one of the diameter of the pupil, the change amount of the pupil diameter, the change speed of the pupil diameter, the reflectivity of the pupil, the visual acuity for viewing a moving object, and the radius of curvature of the cornea, of the eye of the observer.

* * * * *

UNITED STATES PATENT AND TRADEMARK OFFICE
CERTIFICATE OF CORRECTION

PATENT NO. : 5,563,670
DATED : October 8, 1996
INVENTOR(S) : Yoshiharu TENMYO

It is certified that error appears in the above-indentified patent and that said Letters Patent is hereby corrected as shown below:

ON THE COVER PAGE:

[56] References Cited

"U.S. PATENT DOCUMENTS:

"4,619,505  10/1988  Hache et al."
should read
--4,619,505  10/1986  Hache et al.--.

IN THE DRAWING SHEETS:

Sheet 9 of 11:

"WHEN LIGHT" should read --WHEN LIT--.

Sheet 10 of 11:

"FOLLOWING-UP VELOCITY" should read --FOLLOWING-UP VELOCITY)--.

Sheet 11 of 11:

"WHEN LIGHT" should read --WHEN LIT--.

UNITED STATES PATENT AND TRADEMARK OFFICE
CERTIFICATE OF CORRECTION

PATENT NO. : 5,563,670
DATED : October 8, 1996
INVENTOR(S) : Yoshiharu TENMYO

It is certified that error appears in the above-indentified patent and that said Letters Patent is hereby corrected as shown below:

COLUMN 1:

Line 38, "0.2%" should read --0.2%,--.
    Line 60, "an age of the eye" should read --the age of an eye--.

COLUMN 2:

Line 13, "is" should read --has--.
    Line 31, "eye" should read --an eye--.
    Line 40, "eye" should read --an eye--.
    Line 44, "eye" should read --an eye--.
    Line 55, "camera." should read --the camera.--, and "camera" should read --the camera--.
    Line 64, "called as" should read --called--.
    Line 65, "camera" should read --the camera--.
    Line 66, "pupil" should read --the pupil--.

UNITED STATES PATENT AND TRADEMARK OFFICE
CERTIFICATE OF CORRECTION

PATENT NO. : 5,563,670
DATED : October 8, 1996
INVENTOR(S) : Yoshiharu TENMYO

It is certified that error appears in the above-indentified patent and that said Letters Patent is hereby corrected as shown below:

COLUMN 3:

Line 40, "eye." should read --the eye.--.

COLUMN 5:

Line 27, "another" should read --other--.
Line 31, "eye" should read --the eye--.
Line 48, "suffering" should read --suffering from--.

COLUMN 6:

Line 53, "eye" should read --the eye--.
Line 65, "camera." should read --the camera.--.

COLUMN 7:

Line 22, "of" should read --of the--.
Line 38, "lens" should read --the lens--.
Line 40, "of" should read --of the--.
Line 47, "camera" should read --the camera--.
Line 52, "of" should read --of the--.
Line 67, "object, of eye." should read --objects, of the eye.--.

UNITED STATES PATENT AND TRADEMARK OFFICE
CERTIFICATE OF CORRECTION

PATENT NO. : 5,563,670
DATED : October 8, 1996
INVENTOR(S) : Yoshiharu TENMYO

It is certified that error appears in the above-indentified patent and that said Letters Patent is hereby corrected as shown below:

COLUMN 8:

Line 31, "finder," should read --the finder,--.
Line 50, "for" should read --of--.

COLUMN 9:

Line 10, "of a" should read --of the--.
Line 30, "reflected light by eye." should read --light reflected by the eye.--.
Line 31, delete "reflected".
Line 40, "arrows" should read --the arrows--.
Line 44, "arrows" should read --the arrows--.
Line 45, "of" should read --of the--.
Line 60, "optimum for" should read --for--.

COLUMN 10:

Line 2, "object," should read --objects,--.
Line 9, "of," should read --of--.
Line 65, "of," should read --of--.

UNITED STATES PATENT AND TRADEMARK OFFICE
CERTIFICATE OF CORRECTION

PATENT NO. : 5,563,670
DATED : October 8, 1996
INVENTOR(S) : Yoshiharu TENMYO

It is certified that error appears in the above-indentified patent and that said Letters Patent is hereby corrected as shown below:

<u>COLUMN 11</u>:

Line 8, "of" should read --of the--.
Line 9, "of eye" should read --of the eye--.
Line 18, "of" should read --of the--.
Line 21, "axis the" should read --axis of the--.
Line 37, "of" should read --of the--.
Line 48, "of eye" should read --of the eye--.

Signed and Sealed this

First Day of April, 1997

BRUCE LEHMAN

Attest:

Attesting Officer

Commissioner of Patents and Trademarks